United States Patent
Uematsu et al.

(10) Patent No.: US 8,372,630 B2
(45) Date of Patent: Feb. 12, 2013

(54) OPTICAL GLUCOSE SENSOR CHIP AND METHOD OF MANUFACTURING THE SAME

(75) Inventors: Ikuo Uematsu, Yokohama (JP); Masaaki Hirakawa, Yokohama (JP); Kayoko Oomiya, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 278 days.

(21) Appl. No.: 12/771,343

(22) Filed: Apr. 30, 2010

(65) Prior Publication Data

US 2010/0221408 A1 Sep. 2, 2010

Related U.S. Application Data

(63) Continuation of application No. 11/780,033, filed on Jul. 19, 2007, now abandoned.

(30) Foreign Application Priority Data

Jul. 20, 2006 (JP) ................................. 2006-198173

(51) Int. Cl.
*C12M 1/34* (2006.01)
*C12Q 1/54* (2006.01)
*G01N 21/78* (2006.01)

(52) U.S. Cl. ..................... 435/288.7; 435/14; 422/82.11; 436/166; 427/2.13; 385/12

(58) Field of Classification Search ................ 435/287.9, 435/288.7

See application file for complete search history.

(56) References Cited

U.S. PATENT DOCUMENTS

| | | | |
|---|---|---|---|
| 5,456,839 A | 10/1995 | Chou | |
| 5,800,755 A * | 9/1998 | Withenshaw et al. | ........ 264/117 |
| 2006/0134314 A1 | 6/2006 | Kasai et al. | |
| 2006/0198762 A1 | 9/2006 | Uematsu et al. | |
| 2007/0215465 A1 | 9/2007 | Gu | |

FOREIGN PATENT DOCUMENTS

| | | |
|---|---|---|
| EP | 992589 A2 | 4/2000 |
| JP | 2001-508176 | 6/2001 |
| JP | 2006-153497 | 6/2006 |

OTHER PUBLICATIONS

Office Action issued Jan. 25, 2011, in Japan Patent Application No. 2006-198173 (with English translation).
Chen et al., Multifunctional biocompatible membrane and its application to fabricate a miniaturized glucose sensor with potential for use in vivo. Journal of Biomedical Devices. vol. 1 No. 2, pp. 155-166 (1999).
Yu et al, Degradation mechanism of polystyrene sulfonic acid membrane and application of its composite membranes in fuelcells. Phys Chem Chem Phys. Vo. 5. pp. 611-615 (2003).

* cited by examiner

*Primary Examiner* — William H Beisner
(74) *Attorney, Agent, or Firm* — Oblon, Spivak, McClelland, Maier & Neustadt, L.L.P.

(57) ABSTRACT

An optical glucose sensor chip includes a substrate, a pair of optical elements formed on a surface of the substrate for introducing light into the substrate and for emitting the light from the substrate, and a glucose sensing membrane formed on the surface of the substrate at a position between the optical elements. The sensing membrane includes a color reagent substrate, a first enzyme which oxidizes or reduces glucose, a second enzyme that generates a material which makes the color reagent substrate exhibit color by a reaction with a product obtained by oxidation or reduction of glucose, a nonionic cellulose derivative, and an ionic polymer into which a buffer is incorporated. At least one of the first and second enzymes is coated with the ionic polymer, and the color reagent substrate. The first and second enzymes, the buffer and the ionic polymer are supported by the nonionic cellulose derivative.

21 Claims, 2 Drawing Sheets

OPTICAL GLUCOSE SENSOR CHIP AND METHOD OF MANUFACTURING THE SAME

CROSS-REFERENCE TO RELATED APPLICATIONS

This application is based upon and claims the benefit of priority from prior Japanese Patent Application No. 2006-198173, filed Jul. 20, 2006, the entire contents of which are incorporated herein by reference.

BACKGROUND OF THE INVENTION

1. Field of the Invention

The present invention relates to an optical glucose sensor chip and a method of manufacturing the optical glucose sensor chip.

2. Description of the Related Art

As an optical glucose sensor chip, for example, a less invasive type blood sugar level measuring chip has been developed which indirectly measures a blood sugar level by extracting body fluid of subcutaneous tissues. This sensor chip has a structure including a glass substrate, a pair of gratings which are formed on a surface of the substrate and introduce light to or emit the light from the substrate, and a glucose sensing membrane which is positioned between the gratings and formed on the surface of the substrate. This glucose sensing membrane contains a color reagent substrate (for example, 3,3'5,5'-tetramethylbenzidine [TMBZ]), a first enzyme (for example, glucose oxidase [GOD]) that oxidizes or reduces glucose, a second enzyme (for example, peroxidase [POD]) generating a material that reacts with a product obtained by the oxidation or reduction of glucose to make the color reagent substrate exhibit color, and a film forming high-molecular compound (for example, a cellulose derivative such as carboxymethyl cellulose [CMC]).

When a sheet gel is disposed between the skin and the above sensing membrane to apply an electric field in a glucose sensor chip having such a structure, glucose in a subcutaneous tissue solution penetrates the gel from the skin and reaches the above sensing membrane. At this time, the above TMBZ as a color reagent substrate in the sensing membrane makes to exhibit color due to the reaction between glucose and GOD or POD. When light is made to be incident to the above substrate and to be refracted on the surface of the substrate and on one of the above gratings, the light propagates through an interface between the above substrate and the sensing membrane containing color-formed TMBZ, is refracted on the interface between the substrate and the other grating and is received by, for example, a light receiving element. The intensity of the received laser light is less than the intensity (initial intensity) of the laser light received by the light receiving element when the above sensing membrane has not exhibited color. For this reason, the concentration of the above glucose can be detected from the ratio of reduction of the above light intensity.

However, when the above sensing membrane is stored and used for a long time, the activity of the first and second enzymes in the membrane rapidly deteriorates. Examples of the cause of the deterioration include a variation in the pH of the sensing membrane, a variation in the ionic strengths of the first and second enzymes and hydrolysis of the first and second enzymes. When the first and second enzymes deteriorate, the first enzyme reacts insufficiently with glucose which is the subject to be measured. The reduction in the reactivity with glucose reduces the generation of the material that aids the color-forming material obtained by the subsequent reaction with the second enzyme in exhibiting color, with the result that this causes a reduction in the reactivity with the color-forming material and a reduction in the degree of the color to be exhibited, bringing about a deterioration in the sensitivity of the glucose sensor chip.

BRIEF SUMMARY OF THE INVENTION

The present invention is to provide an optical glucose sensor chip which can limit or prevent the deterioration of the first and second enzymes in the sensing membrane with time and to provide a method of manufacturing the optical glucose sensor chip.

According to a first aspect of the present invention, there is provided an optical glucose sensor chip comprising:

a substrate;

a pair of optical elements which formed on a principal surface of the substrate for introducing light into the substrate and for emitting the light from the substrate; and a glucose sensing membrane formed on the principal surface of the substrate at a position between the optical elements;

wherein the sensing membrane includes a color reagent substrate, a first enzyme which oxidizes or reduces glucose, a second enzyme that generates a material which makes the color reagent substrate exhibit color by a reaction with a product obtained by oxidation or reduction of glucose, a nonionic cellulose derivative, and an ionic polymer into which a buffer is incorporated, at least one of the first and second enzymes is coated with the ionic polymer, and the color reagent substrate, the first and second enzymes, the buffer and the ionic polymer are supported by the nonionic cellulose derivative.

According to a second aspect of the present invention, there is provided an optical glucose sensor chip comprising:

a glass substrate;

a pair of optical elements formed on a principal surface of the glass substrate for introducing light into the glass substrate and for emitting the light from the glass substrate;

a light-reflecting path layer formed on the principal surface of the substrate on which the optical elements are formed and made of a resin having a higher refractive index than the substrate; and a glucose sensing membrane formed on the light-reflecting path layer at a position between the optical elements;

wherein the sensing membrane includes a color reagent substrate, a first enzyme which oxidizes or reduces glucose, a second enzyme that generates a material which makes the color reagent substrate exhibit color by a reaction with a product obtained by oxidation or reduction of glucose, a nonionic cellulose derivative, and an ionic polymer into which a buffer is incorporated, at least one of the first and second enzymes is coated with the ionic polymer, and the color reagent substrate, the first and second enzymes, the buffer and the ionic polymer are supported by the nonionic cellulose derivative.

According to a third aspect of the present invention, there is provided a method of manufacturing an optical glucose sensor chip, comprising:

preparing a glucose sensing membrane-forming coating solution by using any of: (a) a method in which at least one of a first enzyme that oxidizes or reduces glucose and a second enzyme that generates a material which makes a color reagent substrate exhibit color by a reaction with a product obtained by oxidation or reduction of glucose is mixed in advance with an aqueous solution containing an ionic polymer and a buffer, and the mixed solution is added to and mixed with the other enzyme, a color reagent substrate and a nonionic cellulose derivative; (b) a method in which the first and second enzymes are respectively mixed in advance with an aqueous solution containing an ionic polymer and a buffer, and the respective prepared mixed solutions are added to and mixed with a color reagent substrate and a nonionic cellulose derivative; or (c) a method in which both the first and second enzymes are mixed in advance with an aqueous solution containing an ionic polymer and a buffer, and the prepared mixed solution is added to and mixed with a color reagent substrate and a nonionic cellulose derivative;

forming a pair of optical elements on a substrate for introducing light into the substrate and for emitting the light from the substrate; and applying the glucose sensing membrane-forming coating solution to a substrate area positioned between the optical elements, followed by drying to form a glucose sensing membrane.

According to a fourth aspect of the present invention, there is provided a method of manufacturing an optical glucose sensor chip, comprising:

preparing a glucose sensing membrane-forming coating solution by using any of: (a) a method in which at least one of a first enzyme that oxidizes or reduces glucose and a second enzyme that generates a material which makes a color reagent substrate develop color by a reaction with a product obtained by oxidation or reduction of glucose is mixed in advance with an aqueous solution containing an ionic polymer and a buffer, and the mixed solution is added to and mixed with the other enzyme, a color reagent substrate and a nonionic cellulose derivative; (b) a method in which the first and second enzymes are respectively mixed in advance with an aqueous solution containing an ionic polymer and a buffer, and the respective prepared mixed solutions are added to and mixed with a color reagent substrate and a nonionic cellulose derivative; or (c) a method in which both the first and second enzymes are mixed in advance with an aqueous solution containing an ionic polymer and a buffer, and the prepared mixed solution is added to and mixed with a color reagent substrate and a nonionic cellulose derivative;

forming a pair of gratings on a substrate for introducing light into the substrate and for emitting the light from the substrate;

forming a light-reflecting path layer made of a resin having a higher refractive index than the substrate on a principal surface of the substrate on which the optical elements are formed; and applying the glucose sensing membrane-forming coating solution to the part of the light-reflecting path layer positioned between the optical elements, followed by drying to form a glucose sensing membrane.

DETAILED DESCRIPTION OF THE INVENTION

An optical glucose sensor chip according to an embodiment of the present invention will be explained in detail with reference to the drawings.

First Embodiment

Figure 1:
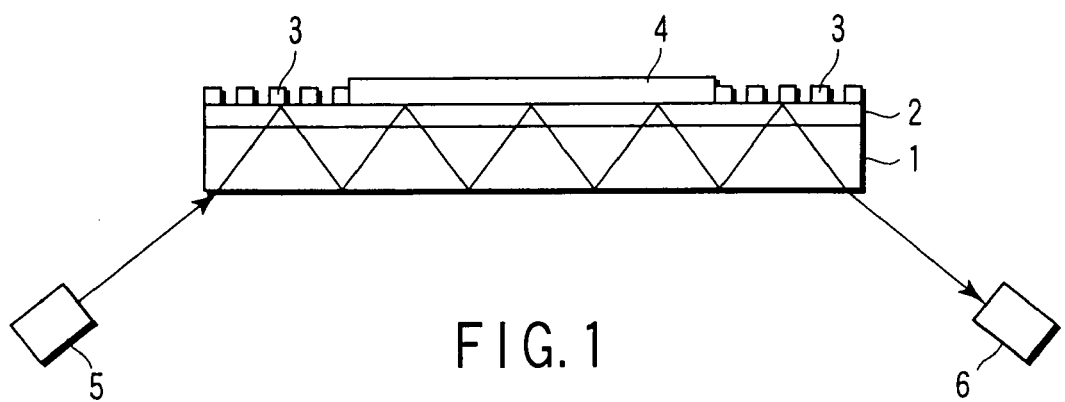
FIG. 1 is a sectional view showing a glucose sensor chip according to a first embodiment.

FIG. 1 is a sectional view showing an optical glucose sensor chip according to a first embodiment.

A glass substrate 1 is provided with a $SiO_2$ surface layer 2 having a thickness of 3 nm or more on its principal surface. A pair of optical elements, for example, a pair of gratings 3 is formed in the vicinities of both ends of the $SiO_2$ surface layer 2 respectively to introduce light into the substrate 1 and to emit the light from the inside of the substrate 1. In this case, the optical elements may be substituted with a prism or the like. These gratings 3 are formed of, for example, titanium oxide having a higher refractive index than the above $SiO_2$ surface layer 2. A protective film having a lower refractive index than the above gratings 3 may be formed so as to coat the gratings 3. This protective film is made of a material, for example, a fluororesin, inert to a chemical solution and a specimen to be used.

A glucose sensing membrane 4 is formed at a position between the gratings 3 on a part of the surface of the $SiO_2$ surface layer 2 of the substrate 1. This glucose sensing membrane 4 includes a color reagent substrate, a first enzyme that oxidizes or reduces glucose, a second enzyme that reacts with a product obtained by oxidizing or reducing glucose to generate a material making the color reagent substrate exhibit color, a nonionic cellulose derivative, and an ionic polymer into which a buffer is incorporated. In the glucose sensing membrane 4, at least one of the above first and second enzymes is coated with the ionic polymer into which the buffer is incorporated. The above color reagent substrate, first and second enzymes, ionic polymer and buffer are supported by the above nonionic cellulose derivative.

Here, the standard for coating at least one of the first and second enzymes with the ionic polymer into which the buffer is incorporated, is determined according to the degree of deterioration with time as explained below.

Specifically, a product obtained by adding glucose to the first enzyme to react is made to act on a specified color reagent substrate, thereby causing the color reagent substrate exhibit color to measure the absorbance at this time. Then, after this first enzyme is exposed to an atmosphere of a fixed temperature and a fixed humidity for a fixed time, a product obtained by adding glucose to the first enzyme to react is made to act on a specified color reagent substrate, thereby causing the color reagent substrate exhibit color to measure the absorbance at this time. The ratio of absorbance reduction between the former and the latter is calculated.

Also, the first and second enzymes are added to glucose and a material produced by a reaction with a product of the first enzyme is made to act on a specified color reagent substrate to cause the color reagent substrate to exhibit color, thereby measuring the absorbance at this time. After the second enzyme is exposed to an atmosphere of a fixed temperature and a fixed humidity for a fixed time in the same manner as in the case of measuring the absorbance of the first enzyme, this second enzyme is added to glucose together with the first enzyme and a material produced by a reaction with a product of the first enzyme is made to act on a specified color reagent substrate to cause the color reagent substrate to exhibit color, thereby measuring the absorbance at this time. The ratio of absorbance reduction between the former and the latter is calculated.

The absorbance reduction ratio due to the deterioration of the first enzyme with time is compared with the absorbance reduction ratio due to the deterioration of the second enzyme with time, to select the one having the larger absorbance reduction ratio, and the selected one is coated with the ionic polymer into which the buffer is incorporated. Also, when the absolute value of the absorbance reduction ratio is large in either the first or second enzyme, it is preferable to coat both with the ionic polymer into which the buffer is incorporated.

The enzyme and color reagent substrate in the glucose sensing membrane 4 are used in the combinations shown in the following Table 1.

TABLE 1

| | First enzyme | Second enzyme | Color reagent substrate |
|---|---|---|---|
| Oxidizing enzyme | Glucose oxidase | Peroxidase | 3,3',5,5'-tetramethylbenzidine<br>N,N'-bis(2-hydroxy-3-sulfopropyl)tolidine<br>3,3'-diaminodenzidine |
| | Hexokinase | Glucose-6-phosphoric acid dehydrogenase | 3-(4,5-dimethyl-2-thiazolyl)-2,5-diphenyl-2H-tetrazolium bromide<br>2-(4-rhodophenyl)-3-(2,4-dinitrophenyl)-5-(2,4-disulfophenyl)-2H-tetrazolium<br>3-3'-[3,3'-dimethoxy-(1,1'-biphenyl)-4,4'-diyl]bis(2,5-diphenyl)-2H-tetrazolium choloride |
| Reducing enzyme | Glucose dehydrogenase | Phosphorus molybdate | Aminobenzoic acid |

The nonionic cellulose derivative used in the glucose sensing membrane 4 is a high-molecular compound participating in the formation of a film. Examples of the nonionic cellulose derivative may include alkyl celluloses such as methyl cellulose and ethyl cellulose; hydroxyalkyl celluloses such as hydroxyethyl cellulose and hydroxypropyl cellulose; hydroxyalkylalkyl celluloses such as hydroxypropylmethyl cellulose, hydroxypropylethyl cellulose, hydroxydiethyl cellulose and hydroxyethylmethyl cellulose; and microfibrous celluloses. These materials may be used either singly or in the form of a mixture.

The above ionic polymer has the function of limiting the precipitation of a salt from the above first and second enzymes during long-term storage and use. This ionic polymer includes a positive ionic polymer and a negative ionic polymer. Examples of the positive ionic polymer include polymers containing a cationic group such as an amino group, guanidino group or biguanide group. Specific examples of the positive ionic polymer include polyallylamine hydrochloride, polyvinylpyridine and polylysine. Examples of the negative ionic polymer include polymers containing an anionic group such as phosphates, carboxylates or sulfonates. Specific examples of the negative ionic polymer include polystyrenesulfonic acid, polyvinylsulfuric acid, polyaspartic acid, polyacrylic acid, polymethacrylic acid, polymaleic acid, polyfumaric acid or cellulose derivatives such as carboxymethyl cellulose and cellulose acetate. Among these ionic polymers, negative ionic polymers are preferable.

The above buffer has the function of controlling the pH and ionic strength of the first and second enzymes to suppress variations in the forms and structures of these enzymes during long-term storage and use. As this buffer, for example, a phosphoric acid buffer, acetic acid buffer, citric acid buffer, boric acid buffer, tartaric acid buffer, trishydrochloric acid buffer or carbonic acid buffer may be used.

At least one of the first and second enzymes is coated with the ionic polymer having incorporated therein such a buffer, whereby not only the precipitation of a salt from the enzyme during long-term storage and use but also variations in the forms and structures of these enzymes are limited to keep these enzymes in highly activated condition.

The above glucose sensing membrane 4 is permitted to contain a crosslinking high-molecular compound. Examples of the crosslinking high-molecular compound may include copolymers of a hydrophilic monomer having at least one group selected from a hydroxyl group, carboxyl group, amino group and ionic functional groups and a hydrophobic monomer.

The copolymer of a hydrophilic monomer and a hydrophobic monomer is preferably a copolymer of 2-methacryloyloxyethylphosphorylcholine and butylacrylate.

The above crosslinking high-molecular compound is preferably contained in the above glucose sensing membrane in an amount of $10^{-4}$ to 10% by weight with respect to all the components of the glucose sensing membrane. When the content of the crosslinking high-molecular compound is less than $10^{-4}$% by weight with respect to all the components of the glucose sensing membrane, it is difficult to prevent the phenomena that the structure of the film is dissolved and broken under heating condition and that the color reagent substrate and enzymes retained in voids in the structure of the film are eluted in an external medium. When the content of the crosslinking high-molecular compound exceeds 10% by weight, on the other hand, there is a fear that the amounts of the color reagent substrate and enzymes in the glucose sensing membrane are relatively reduced and therefore, the sensitivity of the chip is lowered.

The above glucose sensing membrane 4 is permitted to further contain polyethylene glycol or ethylene glycol that provides water permeability in voids in the structure of the film. The glucose sensing membrane 4 containing such polyethylene glycol is increased in hydrophilic properties and it is therefore possible to raise reaction sensitivity when water is used as the medium for introducing glucose.

Next, the action of the optical glucose sensor chip shown in FIG. 1 will be explained.

An adapter (not shown) having a through-hole (well) is brought into contact with a specimen, for example, the skin of a human body and the aforementioned sensor chip is attached to the adapter in such a manner that the glucose sensing membrane 4 is positioned on the well side. This adapter avoids the direct contact of the glucose sensing membrane 4 with the specimen to contribute to the promotion of the reproducibility of the sensing. An extracting medium (for example, a liquid such as water or physiological brine, which does not react directly with the specimen or sensing membrane but has an affinity to them) is filled in the well of the adapter on the side on which the glucose sensing membrane is positioned. Glucose in a skin tissue solution is extracted to the extracting medium from the skin by applying microvoltage to the specimen from the outside and further penetrates the sensing membrane 4 from the extracting medium. When the combination of the first and second enzymes (oxidizing or reducing enzyme) and the color reagent substrate constituting the glucose sensing membrane 4 is, for example, a combination of glucose oxidase (GOD), peroxidase (POD) and 3,3',5,5'-tetramethyl benzidine (TMBZ) shown in the above Table 1, the glucose that has penetrated the sensing membrane 4 is decomposed by GOD to generate hydrogen peroxide, which is then decomposed by POD to emit active oxygen which causes TMBZ to exhibit color. In other words, the chromaticity of TMBZ varies according to the amount of glucose.

In this situation, laser light is made to be incident to the backside of the substrate 1 from the laser light source 5 (for example, a laser diode) through a polar screen (not shown). The incident laser light propagates in the substrate 1 including the $SiO_2$ surface layer 2 while it is refracted at an interface between the $SiO_2$ surface layer 2 of the substrate 1 and the grating 3 on the left and also at an interface between the $SiO_2$ surface layer 2 and the glucose sensing membrane 4 containing the color reagent substrate which has exhibited color. At this time, the evanescent wave of the propagated light is absorbed according to the chromaticity correlated with the amount of glucose contained in the glucose sensing membrane 4. The light propagated in the substrate 1 is emitted from the grating 3 on the right and is received by a light receiving element 6 (for example, a photodiode). The intensity of the received laser light is lower than the intensity (initial intensity) of the laser light received when the color of the sensing membrane 4 is not exhibited. As a result, it is possible to detect the amount of glucose from the ratio of intensity reduction of the laser light.

Next, explanations will be given of a method of manufacturing the optical glucose sensor chip shown in FIG. 1.

First, a coating solution for formation of a glucose sensing membrane is prepared by the following method.

(1) At least one of a first enzyme that oxidizes or reduces glucose and a second enzyme that generates a material which makes a color reagent substrate exhibit color by a reaction with a product obtained by oxidation or reduction of glucose is mixed in advance with an aqueous solution containing an ionic polymer and a buffer. In this mixing process, the above one of the first and second enzymes is coated with the ionic polymer into which the buffer is incorporated. In succession, the mixed solution is added to and mixed with the other enzyme, a color reagent substrate and a nonionic cellulose derivative to prepare a glucose sensing membrane-forming coating solution in which the above one enzyme coated with the ionic polymer is dispersed together with the other enzyme and color reagent substrate in the nonionic cellulose derivative that is a film forming high-molecular compound.

(2) The aforementioned first and second enzymes are respectively mixed in advance in an aqueous solution containing an ionic polymer and a buffer. In this mixing process, the first and second enzymes are coated with the ionic polymer into which the buffer is incorporated. In succession, the prepared two mixed solutions are added to and mixed with a color reagent substrate and a nonionic cellulose derivative to prepare a glucose sensing membrane-forming coating solution in which the above first and second enzymes respectively coated with the ionic polymer are dispersed together with the above color reagent substrate in the nonionic cellulose derivative that is a film forming high-molecular compound.

(3) Both the aforementioned first and second enzymes are mixed in advance in an aqueous solution containing an ionic polymer and a buffer. In this mixing process, the first and second enzymes are coated with the ionic polymer into which the buffer is incorporated. In succession, the prepared mixed solution is added to and mixed with a color reagent substrate and a nonionic cellulose derivative to prepare a glucose sensing membrane-forming coating solution in which the above first and second enzymes coated with the ionic polymer are dispersed together with the above color reagent substrate in the nonionic cellulose derivative that is a film forming high-molecular compound.

Then, a pair of optical elements, for example, gratings, is formed on the substrate. The pair of gratings is formed by the formation of a titanium oxide film on the substrate and by patterning. Successively, the foregoing glucose sensing membrane-forming coating solution is applied to a substrate area positioned between the gratings, followed by drying to form a glucose sensing membrane, thereby manufacturing an optical glucose sensor chip.

As mentioned above, when detecting the amount of glucose by using the optical glucose sensor chip of the first embodiment, at least one of the first and second enzymes in the glucose sensing membrane is coated with the ionic polymer into which the buffer is incorporated. For this reason, during long-term storage and use, the precipitation of a salt from the enzyme can be suppressed and variations in the shape and structure of the enzyme are suppressed to keep the enzyme in highly activated conditions. As a result, it is possible to provide an optical glucose sensor chip which can detect glucose amount in a specimen highly sensitively and stably for a long time.

Also, according to the method of the first embodiment, a glucose sensing membrane-forming coating solution can be prepared in which at least one of the first and second enzymes is coated with the ionic polymer into which the buffer is incorporated and dispersed together with the color reagent substrate in the nonionic cellulose derivative that is a film forming high-molecular compound, by using any of the following methods: (a) at least one of the first enzyme that oxidizes or reduces glucose and the second enzyme that generates a material which makes the color reagent substrate develop color by a reaction with a product obtained by oxidation or reduction of glucose is mixed in advance with an aqueous solution containing the ionic polymer and the buffer, and the mixed solution is added to and mixed with the other enzyme, the color reagent substrate and the nonionic cellulose derivative; (b) the aforementioned first and second enzymes are respectively mixed in advance with an aqueous solution containing the ionic polymer and the buffer, and the respective prepared mixed solutions are added to and mixed with the color reagent substrate and the nonionic cellulose derivative; or (c) both the aforementioned first and second enzymes are mixed in advance with an aqueous solution containing the ionic polymer and the buffer, and the prepared mixed solution is added to and mixed with the color reagent substrate and the nonionic cellulose derivative. Thereafter, a pair of gratings is formed on the substrate and the foregoing glucose sensing membrane-forming coating solution is applied to a substrate area positioned between the gratings, followed by drying to form a glucose sensing membrane, thereby manufacturing an optical glucose sensor chip which can detect glucose amount in a specimen highly sensitively and stably for a long time.

Second Embodiment

Figure 2:
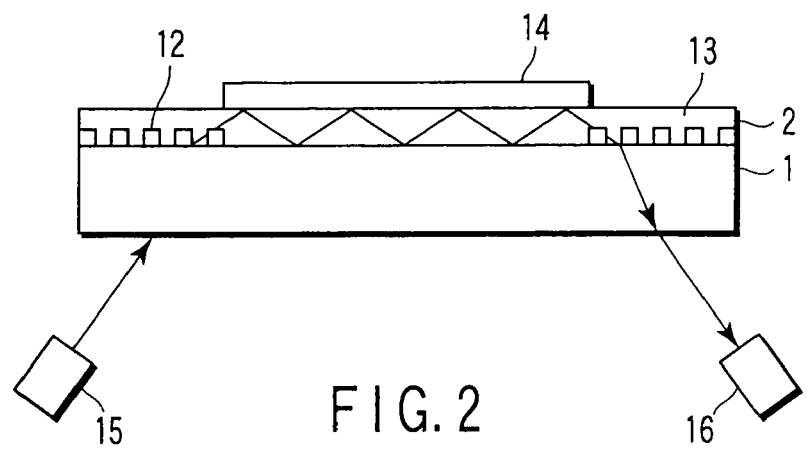
FIG. 2 is a sectional view showing a glucose sensor chip according to a second embodiment.

FIG. 2 is a sectional view showing an optical glucose sensor chip according to a second embodiment.

A pair of gratings 12 which are optical elements is formed on the principal surface of a glass substrate 11 in the vicinities of both ends of the substrate 11 to introduce light into the substrate 11 and to emit the light from the substrate 11, respectively. These gratings 12 are made of, for example, titanium oxide having a higher refractive index than the above substrate 11. A light-reflecting path layer 13 formed of a heatcurable or photocurable resin having a higher refractive index than the substrate 11 is formed on the principal surface of the substrate 11 including the gratings 12. The principal surface of the light-reflecting path layer 13 is formed in parallel to the principal surface of the substrate 11 including the gratings 12.

A glucose sensing membrane 14 is formed on the part above the light-reflecting path layer 13 positioned between the gratings 12. This glucose sensing membrane 14 has the same structure as that of the first embodiment, that is, the structure in which at least one of a first enzyme that oxidizes or reduces glucose and a second enzyme that generates a material which makes a color reagent substrate exhibit color by a reaction with a product obtained by oxidation or reduction of glucose is coated with an ionic polymer into which a buffer is incorporated, and these enzymes, ionic polymer, buffer and color reagent substrate are supported by the nonionic cellulose derivative.

Here, the standard for coating at least one of the first and second enzymes with the ionic polymer into which the buffer is incorporated, is the same as that explained in the above first embodiment.

The above light-reflecting path layer 13 preferably has a smooth surface and a thickness of 10 μm or more and more preferably 10 to 200 μm. A light-reflecting path layer having a thickness of 10 μm or more makes it possible to limit a decay of light intensity when light is propagated and to use, for example, a LED light source in addition to a laser light.

The first and second enzymes and color reagent substrate in the above glucose sensing membrane 14 are used in the combinations shown in the above Table 1.

As the ionic polymer, buffer and nonionic cellulose derivative in the glucose sensing membrane 14, the same ones exemplified in the above first embodiment may be used.

The above glucose sensing membrane 14 may further contain a crosslinking high-molecular compound and may also contain polyethylene glycol or ethylene glycol as explained in the above first embodiment.

Next, the action of the optical glucose sensor chip shown in FIG. 2 will be explained.

An adapter (not shown) having a through-hole (well) is brought into contact with a specimen, for example, the skin of a human body and the aforementioned sensor chip is attached to the adapter in such a manner that the glucose sensing membrane 14 is positioned on the well side. An extracting medium including water is filled in the well of the adapter on the side on which the glucose sensing membrane is positioned. Glucose in a skin tissue solution is extracted to the extracting medium from the skin by applying microvoltage to the specimen from the outside and further penetrates the sensing membrane 14. When the combination of the first and second enzymes (oxidizing or reducing enzyme) and the color reagent substrate constituting the glucose sensing membrane 14 is, for example, a combination of glucose oxidase (GOD), peroxidase (POD) and 3,3',5,5'-tetramethyl benzidine (TMBZ) shown in the above Table 1, the glucose that has penetrated the sensing membrane 14 is decomposed by GOD to generate hydrogen peroxide, which is then decomposed by POD to emit active oxygen which causes TMBZ to exhibit color. In other words, the chromaticity of TMBZ varies according to the amount of glucose.

In this situation, laser light is made to be incident to the backside of the substrate 11 from the laser light source 15 (for example, a laser diode) through a polar screen (not shown). The laser light passes through the substrate 11 and is refracted at an interface between the principal surface of the substrate 11 and the grating 12 on the left, whereby the light is incident to an optical waveguide layer 13. The light is also refracted at an interface between the optical waveguide layer 13 and the glucose sensing membrane 14 containing the color reagent substrate which has exhibited color to propagate in the optical waveguide layer 13. At this time, the evanescent wave of the propagated light is absorbed according to the chromaticity correlated with the amount of glucose contained in the glucose sensing membrane 14. The light propagated in the optical waveguide layer 13 is emitted from the grating 12 on the right and is received by a light receiving element 16 (for example, a photodiode). The intensity of the received laser light is lower than the intensity (initial intensity) of the laser light received when the color of the sensing membrane 14 is not exhibited. As a result, it is possible to detect the amount of glucose from the ratio of intensity reduction of the laser light.

Next, explanations will be given of a method of manufacturing the optical glucose sensor chip shown in FIG. 2.

First, by using any of the same three methods that are explained in the first embodiment, a coating solution for formation of a glucose sensing membrane is prepared in which at least one of the first and second enzymes is coated in advance with the ionic polymer into which the buffer is incorporated and dispersed together with the color reagent substrate in the nonionic cellulose derivative that is a film forming high-molecular compound.

Then, a pair of optical elements, for example, gratings is formed on the principal surface of the glass substrate. The pair of gratings is formed by the formation of a titanium oxide film on the glass substrate and by patterning. Successively, a light-reflecting path layer made of a heatcurable or photocurable resin having a higher refractive index than the substrate is formed on the principal surface of the substrate on the side formed with the grating. Then, the foregoing glucose sensing membrane-forming coating solution is applied to the part of the light-reflecting path layer positioned between the gratings, followed by drying to form a glucose sensing membrane, thereby manufacturing an optical glucose sensor chip.

As mentioned above, when detecting the amount of glucose by using the optical glucose sensor chip of the second embodiment, at least one of the first and second enzymes in the glucose sensing membrane is coated with the ionic polymer into which the buffer is incorporated in the same manner as in the first embodiment. For this reason, during long-term storage and use, the precipitation of a salt from the enzyme can be suppressed and variations in the shape and structure of the enzyme are suppressed to keep the enzyme in highly activated conditions. As a result, it is possible to provide an optical glucose sensor chip which can detect glucose amount in a specimen highly sensitively and stably for a long time.

Also, according to the second embodiment, a glucose sensing membrane-forming coating solution can be prepared in which at least one of the first and second enzymes is coated with the ionic polymer into which the buffer is incorporated and dispersed together with the color reagent substrate in the nonionic cellulose derivative that is a film forming high-molecular compound. Thereafter, a pair of gratings is formed on the principal surface of the glass substrate, a light-reflecting path layer having a higher refractive index than the substrate is formed on the principal surface of the substrate on the side formed with the gratings, and the foregoing glucose sensing membrane-forming coating solution is applied to between the gratings above the light-reflecting path layer, followed by drying to form a glucose sensing membrane, thereby manufacturing an optical glucose sensor chip which can detect glucose amount in a specimen highly sensitively and stably for a long time.

The present invention will be explained by way of examples.

EXAMPLE 1

Nine μL of a mixture solution of a 0.67 mg/mL peroxidase (POD) solution (dissolved in a 0.01 mol/L phosphoric acid buffer solution [pH: 6.0]) and a 5.33 mg/mL glucose oxidase (GOD) solution (dissolved in a 0.01 mol/L phosphoric acid buffer solution [pH: 6.0]) was mixed in 1 μL of an aqueous 1 wt % carboxymethyl cellulose (CMC) (negative ionic polymer) solution and the mixture was stirred. Nine μL of the obtained mixture solution was added to 143.6 μL of isopropyl alcohol (IPA), 116.6 μL of purified water, 6 μL of an isopropyl alcohol solution containing 1% by volume of polyethylene glycol (PEG), 60 μL of an isopropyl alcohol solution containing 1 mg/mL of 3,3',5,5'-tetramethylbenzidine (TMBZ), 64 μL of an aqueous 2 wt % hydroxyethyl cellulose (HEC) solution and 0.8 μL of an aqueous crosslinking high-molecular compound (2-methacryloyloxyethylphosphorylcholine/butylmethacrylate copolymer) solution and these components were mixed and stirred to prepare 400 μL of a glucose sensing membrane-forming coating solution.

Next, a non-alkali glass substrate which was provided with a $SiO_2$ surface layer having a thickness of 10 nm on its principal surface and had a refractive index of 1.52 was prepared. A titanium oxide film having a thickness of 50 nm and a refractive index of 2.2 to 2.4 was formed on the $SiO_2$ surface layer of this substrate by sputtering. In succession, a resist was applied to the titanium oxide film and dried, and then a resist pattern was formed by lithography. Then, by using the resist pattern as a mask, the titanium oxide film was selectively removed by reactive ion etching (RIE), thereby forming gratings on the $SiO_2$ surface layer in the vicinity of each end of the surface. Then, the resist pattern was removed by ashing.

Next, the above substrate was dry-cleaned by oxygen RIE and then cut into a chip form having a size of 17 mm×6.5 mm. Then, 8 μl, of the above glucose sensing membrane-forming coating solution was dripped on the surface of a sensing membrane forming area positioned between the gratings of the substrate, and dried by purging using inert gas and vacuum drying, thereby forming a porous (water permeable) glucose sensing membrane 0.8 μm in thickness. In this manner, an optical glucose sensor chip shown in the above FIG. 1 was manufactured. A liquid droplet of the glucose sensing membrane-forming coating solution to be dripped had the following composition.

Phosphoric acid buffer solution: 0.000525 mol/L
Phosphoric acid buffer solution: 0.0003 mol/L
PEG: 0.15% by volume
TMBZ: 0.15 mg/dL
POD: 0.0015 mg/mL
GOD: 0.012 mg/mL
CMC (negative ionic polymer): 0.0005% by weight
HEC: 0.64% by weight
2-Methacryloyloxyethylphosphorylcholine and butylmethacrylate copolymer: 0.002% by weight

EXAMPLE 2

An optical glucose sensor chip shown in the above FIG. 1 was produced by forming a sensing membrane in the same manner as in Example 1 except that polylysine as a positive ionic polymer was blended in the droplet of the glucose sensing membrane-forming coating solution in an amount of 0.0008 μg/L in place of CMC as a negative ionic polymer in Example 1.

COMPARATIVE EXAMPLE 1

An optical glucose sensor chip shown in the above FIG. 1 was produced by forming a sensing membrane in the same manner as in Example 1 by using a glucose sensing membrane-forming coating solution prepared by one mixing operation using the same components as in Example 1 except that the ionic polymer and the sodium phosphate buffer were not contained.

With regard to the optical glucose sensor chips obtained in Examples 1 and 2 and Comparative Example 1, a variation in sensitivity (absorbance) to glucose with time was measured using the following method.

Specifically, an adapter having a through-hole (well) was brought into contact with a proper flat plate (for example, a glass plate). Each sensor chip was attached to this adapter in such a manner that the glucose sensing membrane was disposed on the well side to partition the well. In the situation (temperature: 35° C.) where an aqueous solution containing 1 mg/dL of glucose was filled in the well, laser light was made to be incident to the backside of the substrate 1 from a laser diode 5 through a polar screen as shown in FIG. 1. The incident laser light was refracted at an interface between the $SiO_2$ surface layer 2 of the substrate 1 and the grating 3 on the left, and also refracted at an interface between the $SiO_2$ surface layer 2 and the glucose sensing membrane 4 containing the color reagent substrate which had exhibited color to propagate in the substrate 1 including the $SiO_2$ surface layer 2. The laser light propagated by the refraction at an interface between the grating 3 on the right and the substrate 1 was received by a photodiode 6 to measure the intensity (absorbance) of the received laser light.

The same operations as above were carried out after the sensor chip had been stored for one day, 14 days, 40 days and 100 days in the case of the sensor chips of Examples 1 and 2 respectively and after the sensor chip had been stored for one day, 7 days and 90 days in the case of the sensor chip of Comparative Example 1.

Figure 3:
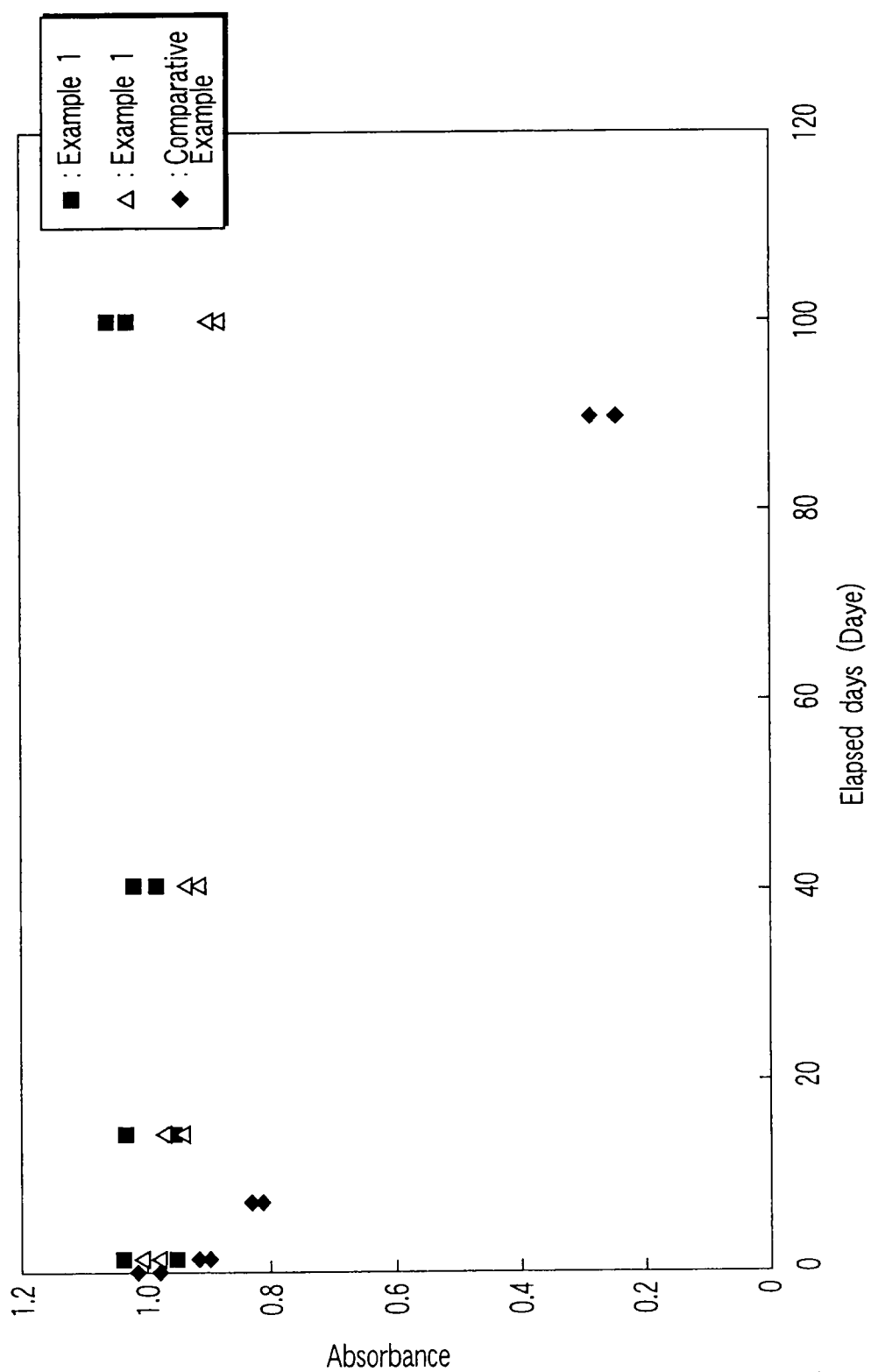
FIG. 3 is a view showing a variation in the absorbance (sensitivity) of a glucose sensor chip of each of Examples 1 and 2 and Comparative Example 1 with the passage of a storage time.

The results of these operations are shown in FIG. 3.

As can be understood from FIG. 3, the sensitivity of the sensor chip of Comparative Example 1 deteriorates more after the chip has been stored for 7 days and more significantly after the chip has been stored for 90 days compared with the sensitivity obtained before the sensor is stored.

It can be understood, on the other hand, that each sensor chip of Examples 1 and 2 has a sensitivity similar to that obtained before the sensor chip is stored even after the sensor chip has been stored for 100 days. It is found that, particularly, the sensor chip of Example 1 provided with a glucose sensing membrane containing a negative ionic polymer has a higher capability of maintaining sensitivity with the passage of storage time than that of Example 2 provided with a glucose sensing membrane containing a positive ionic polymer.

Similarly to Example 1, the glucose sensor chip shown in FIG. 2 provided with a light-reflecting path layer made of a heatcurable or photocurable resin having a higher refractive index than the substrate could maintain high sensitivity even after being stored for a long time.

Also, as each of the first enzyme, second enzyme and color reagent substrate supported by the glucose sensing membrane used in the above embodiments and examples, only one material is selected. However, plural materials may be combined according to the purpose of use.

Moreover, glass is used as the substrate in the above embodiment. However, no restriction is imposed on this material as long as it has the characteristics allowing reference light to propagate and be transmitted. Film bodies of single crystals and various resin materials may also be used, such as heatcurable resin materials, thermoplastic resin materials and photocurable resin materials.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an optical glucose sensor chip, comprising:
   preparing a glucose sensing membrane-forming coating solution that comprises:
   a color reagent substrate;
   a first enzyme that oxidizes or reduces glucose;
   a second enzyme that generates a material which makes the color reagent substrate exhibit color by a reaction with a product obtained by the oxidation or reduction of glucose;
   a nonionic cellulose derivative;
   an ionic polymer selected from the group consisting of a polymer containing a cationic group which is an amino group, guanidino group or biguanide group, and a polymer containing an anionic group which is a phosphate group or sulfonate group; and
   a buffer;
   by using any of:
   (a) a method in which
   either the first enzyme or the second enzyme is mixed in advance with an aqueous solution containing the ionic polymer and the buffer, and the mixed solution is added to and mixed with the other enzyme, the color reagent substrate and the nonionic cellulose derivative;
   (b) a method in which the first and second enzymes are respectively mixed in advance with an aqueous solution containing the ionic polymer and the buffer, and the respective prepared mixed solutions are added to and mixed with the color reagent substrate and the nonionic cellulose derivative; or
   (c) a method in which both the first and second enzymes are mixed in advance with an aqueous solution containing the ionic polymer and the buffer, and the prepared mixed solution is added to and mixed with the color reagent substrate and the nonionic cellulose derivative;
   forming a pair of optical elements on a substrate for introducing light into the substrate and for emitting the light from the substrate; and
   applying the glucose sensing membrane-forming coating solution to a substrate area positioned between the optical elements, followed by drying to form a glucose sensing membrane.

2. The method of claim 1, comprising preparing a glucose sensing membrane-forming coating solution by (a) a method in which
   either the first enzyme or the second enzyme is mixed in advance with an aqueous solution containing the ionic polymer and the buffer, and the mixed solution is added to and mixed with the other enzyme, the color reagent substrate and the nonionic cellulose derivative.

3. The method of claim 1, comprising preparing a glucose sensing membrane-forming coating solution by (b) a method in which the first and second enzymes are respectively mixed in advance with an aqueous solution containing the ionic polymer and the buffer, and the respective prepared mixed solutions are added to and mixed with the color reagent substrate and the nonionic cellulose derivative.

4. The method of claim 1, comprising preparing a glucose sensing membrane-forming coating solution by (c) a method in which both the first and second enzymes are mixed in advance with an aqueous solution containing an ionic polymer and a buffer, and the prepared mixed solution is added to and mixed with a color reagent substrate and a nonionic cellulose derivative.

5. The method according to claim 1, wherein the first enzyme is glucose oxidase, the second enzyme is peroxidase and the color reagent substrate is at least one of 3,3,5,5-tetramethylbenzidine and N,N'-bis(2-hydroxy-3-sulfopropyl)tridine.

6. The method according to claim 1, wherein the nonionic cellulose derivative is at least one selected from the group consisting of an alkyl cellulose, a hydroxyalkyl cellulose and a hydroxyalkylalkyl cellulose.

7. The method according to claim 1, wherein the sensing membrane further contains a crosslinking high-molecular compound.

8. The method according to claim 7, wherein the crosslinking high-molecular compound is a copolymer of a hydrophobic monomer and a hydrophilic monomer having at least one group selected from the group consisting of a hydroxyl group, a carboxyl group, an amino group and an ionic functional group.

9. The method according to claim 8, wherein the copolymer of a hydrophilic monomer and a hydrophobic monomer is a copolymer of 2-methacryloyloxyethylphosphorylcholine and butylmethacrylate.

10. The method according to claim 1, wherein the glucose sensing membrane further contains polyethylene glycol or ethylene glycol for endowing the membrane with water permeability.

11. The method of claim 1, wherein the ionic polymer comprises a cationic group which is a guanidino group or a biguanide group.

12. The method of claim 1, wherein the ionic polymer comprises an anionic group which is a phosphate group or sulfonate group.

13. A method of manufacturing an optical glucose sensor chip, comprising:
   preparing a glucose sensing membrane-forming coating solution that comprises:
   a color reagent substrate;
   a first enzyme that oxidizes or reduces glucose;
   a second enzyme that generates a material which makes the color reagent substrate exhibit color by a reaction with a product obtained by the oxidation or reduction of glucose;
   a nonionic cellulose derivative;
   an ionic polymer selected from a polymer containing a cationic group which is an amino group, guanidino group or biguanide group; and a polymer containing an anionic group which is a phosphate group or a sulfonate group; and
   a buffer;
   by using any of:
   (a) a method in which
   either the first enzyme or the second enzyme is mixed in advance with an aqueous solution containing the ionic polymer and the buffer, and the mixed solution is added to and mixed with the other enzyme, the color reagent substrate and the nonionic cellulose derivative;

(b) a method in which the first and second enzymes are respectively mixed in advance with an aqueous solution containing the ionic polymer and the buffer, and the respective prepared mixed solutions are added to and mixed with the color reagent substrate and the nonionic cellulose derivative; or (c) a method in which both the first and second enzymes are mixed in advance with an aqueous solution containing the ionic polymer and the buffer, and the prepared mixed solution is added to and mixed with the color reagent substrate and the nonionic cellulose derivative;

forming a pair of gratings on a substrate for introducing light into the substrate and for emitting the light from the substrate;

forming a light-reflecting path layer made of a resin having a higher refractive index than the substrate on a principal surface of the substrate on which the optical elements are formed; and applying the glucose sensing membrane-forming coating solution to the part of the light-reflecting path layer positioned between the optical elements, followed by drying to form a glucose sensing membrane.

14. The method according to claim 13, wherein the first enzyme is glucose oxidase, the second enzyme is peroxidase and the color reagent substrate is at least one of 3,3,5,5-tetramethylbenzidine and N,N'-bis(2-hydroxy-3-sulfopropyl)tridine.

15. The method according to claim 13, wherein the nonionic cellulose derivative is at least one selected from the group consisting of an alkyl cellulose, a hydroxyalkyl cellulose and a hydroxyalkylalkyl cellulose.

16. The method according to claim 13, wherein the sensing membrane further contains a crosslinking high-molecular compound.

17. The method according to claim 16, wherein the crosslinking high-molecular compound is a copolymer of a hydrophobic monomer and a hydrophilic monomer having at least one group selected from the group consisting of a hydroxyl group, a carboxyl group, an amino group and an ionic functional group.

18. The method according to claim 17, wherein the copolymer of a hydrophilic monomer and a hydrophobic monomer is a copolymer of 2-methacryloyloxyethylphosphorylcholine and butylmethacrylate.

19. The method according to claim 13, wherein the glucose sensing membrane further contains polyethylene glycol or ethylene glycol for endowing the membrane with water permeability.

20. The method of claim 13, wherein the ionic polymer comprises a cationic group which is a guanidino group or a biguanide group.

21. The method of claim 13, wherein the ionic polymer comprises an anionic group which is a phosphate group or sulfonate group.

* * * * *